United States Patent [19]

Clark

[11] 4,363,327
[45] Dec. 14, 1982

[54] CYCLIC INJECTION METHOD FOR CONTINUOUS MEASUREMENTS OF PULMONARY PARAMETERS

[75] Inventor: Justin S. Clark, Salt Lake City, Utah

[73] Assignee: Intermountain Health Care, Salt Lake City, Utah

[21] Appl. No.: 180,369

[22] Filed: Aug. 22, 1980

[51] Int. Cl.³ .............................................. A61B 5/08
[52] U.S. Cl. .................................... 128/719; 128/691
[58] Field of Search .................... 128/716, 718–720, 128/724–725, 691

[56] References Cited

U.S. PATENT DOCUMENTS

| | | | |
|---|---|---|---|
| 3,622,059 | 11/1971 | Sarela | 101/348 X |
| 4,034,743 | 7/1977 | Greenwood et al. | 128/725 |
| 4,083,367 | 4/1978 | Portner et al. | 128/691 |
| 4,169,465 | 10/1979 | Walls et al. | 128/719 |
| 4,207,818 | 6/1980 | Hamisch, Jr. | 101/348 |
| 4,221,224 | 9/1980 | Clark | 128/725 X |
| 4,301,729 | 11/1981 | Fujita | 101/348 X |

OTHER PUBLICATIONS

Kirsch, Raymond C., "Snap-On Idler Roll", Xerox Disclosure Journal, vol. 5, No. 1, Jan./Feb. 1980.
Howard, R. P. et al., "Computerized Cardiopulmonary Stress Testing in Children", IEEE Publ. CH1480, 3/79-0648, 1979.
Wessel, H. U. et al., "Minicomputer Based System for Breath by Breath Analysis of Ventilation and Pulmonary Gas Exchange", IEEE Publ. CH1391-2/78-0000.
Wagner, P. D. et al., "Measurement of Continuous Distributions of Ventilation-Perfusion Ratios: Theory", Jrnl. Appl. Phys., vol. 36, #5, May 1974, pp. 588–599.
Barrow, R. E., "Method of Measuring Human Pulmonary Capillary Blood Flow", Med. & Biol. Engrg., vol. 14, No. 5, pp. 538–544, Sep. 1976.

*Primary Examiner*—Lee S. Cohen
*Assistant Examiner*—Francis J. Jaworski
*Attorney, Agent, or Firm*—Thorpe, North & Western

[57] ABSTRACT

A non-invasive cyclic injection method for determining pulmonary blood flow, the ventilation-perfusion distribution and functional residual capacity, which consists of the non-invasive cyclical introduction of soluble and insoluble inert gases into the airstream of the human patient, each period of introduction followed by a similar period free from the introduction of soluble inert gases to allow for the washout of their concentrated buildup in the venous system. Sampling and analysis of expired air during all parts of the cyclic injection and non-injection of gases takes place with the results being electronically obtained and translated into digital data indicative of the parameter being determined.

17 Claims, 5 Drawing Figures venous return gas fraction venous return gas fraction cyclic alveolar gas fraction

CYCLIC INJECTION METHOD FOR CONTINUOUS MEASUREMENTS OF PULMONARY PARAMETERS

BACKGROUND OF THE INVENTION

This invention deals with the cyclic non-invasive introduction of soluble and insoluble inert gases into the airway of a human patient for purposes of obtaining continuous measurements of such pulmonary parameters as pulmonary blood flow, ventilation-perfusion distribution and functional residual capacity.

In existing theory and practice, gas exchange of soluble inert gas to determine pulmonary blood flow ($Q_c$) has been used. However, the earlier techniques contained certain inherent problems as to the manner of injection and sampling of the soluble gases. For example, with the plethysmographic and rebreathing methods, a willing and cooperative patient is required for achieving best results. This limits the usefulness for testing of neonates, young children, and patients who are unconscious or unwilling to participate. The rebreathing method has the additional disadvantage of requiring an airtight system. In addition, it cannot be used continuously to monitor a patient's condition due to recirculation of the soluble inert gas. Another major problem with the breath holding and rebreathing techniques is that they disturb the parameters being measured. A third major problem is that both the rebreathing and breath-holding techniques are based on a uniform or homogeneous model of the lung. This representation is not usually valid for patients with significant pulmonary disease.

A method for measuring the ventilation-perfusion distribution requires continuous intravenous injections of soluble gases of differing solubilities as well as periodic sampling from the central venous system. Blood sampling requires the use of a catheter which passes into the pulmonary system through the heart. Not only is this method highly invasive but is is noncontinuous as well. Therefore, the range of practical usefulness of the method is very limited.

It would be of great value to obtain such parameters as pulmonary blood flow, the ventilation-perfusion distribution, and functional residual capacity (FRC) by non-invasive means which require minimal or no patient cooperation. Among those with pulmonary diseases, continuous monitoring of such parameters would be an important and helpful means of diagnosis and treatment. For example: reduced pulmonary blood flow could indicate PFC (persistant fetal circulation) in a neonate, a decrease in FRC (functional residual capacity) might indicate collapsed alveoli present in RDS (Respiratory Distress Syndrome) patients, and significant ventilation in high $\dot{V}/\dot{Q}$ regions could indicate improper mechanical ventilation or the presence of pulmonary emboli.

The importance of these parameters in the diagnosis and treatment of ill patients, many of whom could be uncooperative is apparent. There is also a use and reason for knowing and obtaining such parameters in normals. The growing number of health spas and the importance placed on exercising creates a use for testing to determine such parameters as pulmonary blood flow ($Q_c$), oxygen uptake, and carbon dioxide production. Such knowledge could lead to better exercise programs and would lead to a better characterization of a healthy physique and its parameters. Overall, there is a need to develop and employ a non-invasive method of continuously monitoring and measuring the above mentioned pulmonary parameters.

OBJECTS AND SUMMARY OF THE INVENTION

It is an object of the present invention to provide a method for determining pulmonary blood flow, the ventilation perfusion distribution and functional residual capacity by the cyclical introduction of soluble and insoluble inert gases into an airway of the patient accompanied by the sampling and analysis of expired gases.

It is also an object of this invention to provide a method for determining lung parameters which will eliminate errors due to the recirculation of the soluble trace gas through venous return blood flow by introducing the soluble gases cyclically, which introduction is for a given period followed by a similar period of time with no introduction allowing for a washout and achieving steady-state to minimize such errors.

It is also an object of this invention to non-invasively inject soluble and insoluble gases into a patient upon inhalation for a given number of breaths, followed by a similar number of breaths taken without introduction of said gases, such a method being called a cyclical injection method, in order to determine the pulmonary blood flow.

These and other objects may be accomplished by non-invasively injecting at least one insoluble gas and one or more soluble gases into the patient during inhalation over a given period of time which preferably consists of a given number of breaths. The continuous cyclic periods of injection followed by similar periods of non-injections requires continuous sampling and monitoring of gases of exhaled air. Such monitored data is electronically transformed into digital data relating to those pulmonary parameters desired. This data may confirm the health of a patient or be used for effective diagnosis and treatment of ill patients. Although it is preferable, the exact volume and/or amount of injected soluble gases need not be known as long as the ratio of soluble to insoluble gases is given.

DETAILED DESCRIPTION OF THE DRAWINGS

This invention relates to a method of determining such pulmonary parameters as pulmonary blood flow ($Q_c$), the ventilation-perfusion distribution and functional residual capacity (FRC) by cyclically introducing soluble and insoluble gases into the lungs and monitoring exhaled gases. The insoluble gas is introduced for purposes of determining the alveolar ventilation ($\dot{V}_A$).

Given the amount of insoluble gas inspired and measuring the amount expired after equilibrium is reached, it is relatively simple to determine the alveolar ventilation ($\dot{V}_A$) as detailed in U.S. Pat. No. 4,226,224 filed June 29, 1978. If the volume per unit time of expired helium is given by $\dot{V}_{He}$, where helium is the insoluble gas, then this volume is equal to the total expired alveolar volume per unit time ($\dot{V}_A$) multiplied by the fraction of expired alveolar gas which is helium ($F_{AHe}$). It is also known that the rate of expiration of helium, where equilibrium is reached, is equal to the rate of helium inspiration ($\dot{V}_{IHe}$) which is known and given. Therefore, these relationships may be expressed by the following equation:

$$\dot{V}_{IHe} = \dot{V}_{He} = \dot{V}_A \times F_{AHe}$$

Departing from U.S. Pat. No. 4,221,224, the improved method introduces an insoluble gas as well as several soluble gases to the subject in a cyclic fashion. The analysis of the expired profile of one soluble gas provides the information for determining the $\dot{Q}_c/\dot{V}_A$ ratio (applicable to a uniform lung), which when multiplied by $\dot{V}_A$ (obtained by analysis of the insoluble gas) provides the measurement of pulmonary blood flow ($\dot{Q}_c$). As with other inert gas methods referred to previously, this method is based on the principle that a soluble gas is removed from the lung at a rate proportional to the pulmonary blood flow multiplied by the gas fraction and solubility of the gas in blood. The uniqueness of this method is the manner in which recirculation of the soluble gas (gases) is handled. This recirculation called venous return limits other methods to single measurements made rapidly before the uncertainty of venous concentrations disturb the mass balance equations. This method, based on a cyclic injection pattern, is indifferent to unknown but slowly varying concentrations of soluble gases in the venous system, a concept which allows the method to be applied repetitively or near continuously. Gas introduction and sampling is accomplished during normal breathing. This removes requirements of patient cooperation and causes no change of the physiological parameters being measured.

Figure 1:
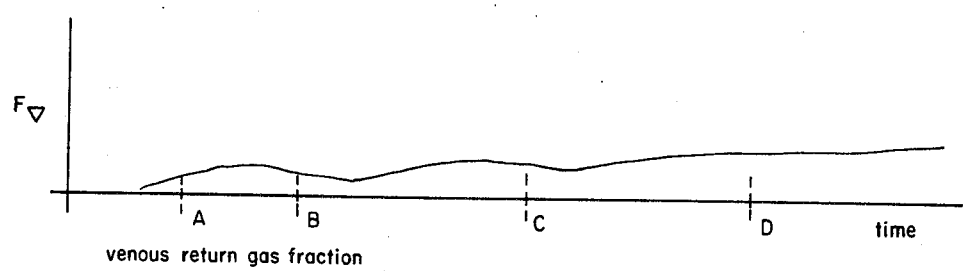
FIG. 1 is a plot of the venous return gas fraction, with respect to time, of a soluble gas over a number of cycles.

Cyclical soluble gas injections, according to the present invention, produce significant venous return of the soluble gases; however, only the changes in venous concentration over the cycle period give rise to error. Such changes become small as a cyclic steady state is approached as shown by FIG. 1.

Figure 2:
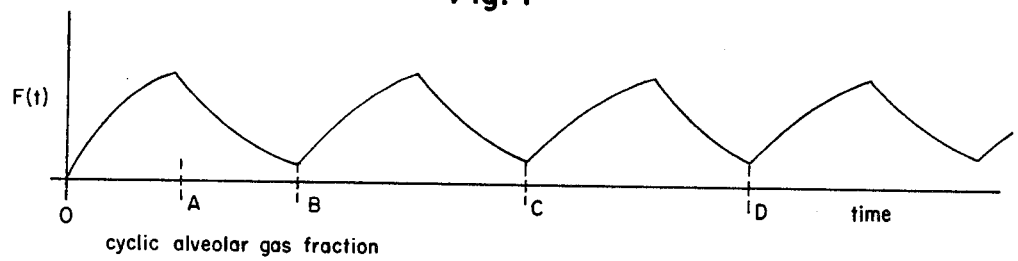
FIG. 2 is a plot of the cyclic alveolar gas fraction of a soluble gas showing washin and washout concentrations for a given cycle period.
Figure 3:
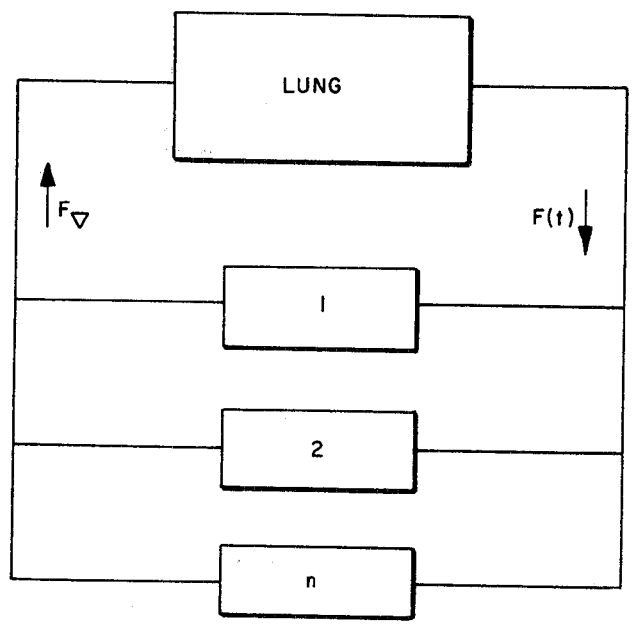
FIG. 3 is a simplified circulation model of the lung and vascular bed with circulation paths 1, 2, n for each of the parallel vascular bed branches.

The reason for the reduction in error due to venous return as the cyclic steady state is approached is as follows: The alveolar gas fraction (F(t)), as shown in FIG. 2 is cyclic and can, therefore, be represented mathematically as a series of sine functions of varying amplitudes, frequencies and phases. Each frequency component is the input to a parallel network of circulation pathways as shown in FIG. 3, each of which provide an output gas fraction component which has a characteristic attenuation and phase shift for each frequency component. The mixed venous return gas fraction is the algebraic sum of the outputs from each pathway. Because numerous pathways exist, having a somewhat randomized phase shift characteristic, significant cancellation of the cyclic components occurs after several cycles. Therefore, the error due to venous return is reduced if F(t) is cycled many times rather than using a single transient. In prior art methods, the time average of the venous concentration produces unaccountable error, while in the cyclic method, only the ripple in the venous concentration (See FIG. 1) produces unaccountable error. Most of the ripple is filtered by passage through the systemic system.

Although the invention does not require the solving of a particular algorithm, it is to be realized that the obtaining of cyclic soluble gas fraction patterns such as shown in FIG. 2 for one or more expired soluble gases is only a function of the ventilation-perfusion ratio ($\dot{V}/\dot{Q}$) (to be shown in the following paragraph) which must be mathematically interpreted. The use of an insoluble gas and a single soluble gas provides data for a one-compartment (uniform) lung model. With the monitoring of additional soluble gases, the lung may be modeled with additional $\dot{V}/\dot{Q}$ compartments. Thus, with enough gases, a profile of ventilation is obtained as a function of the ventilation-perfusion distribution.

Figure 4:
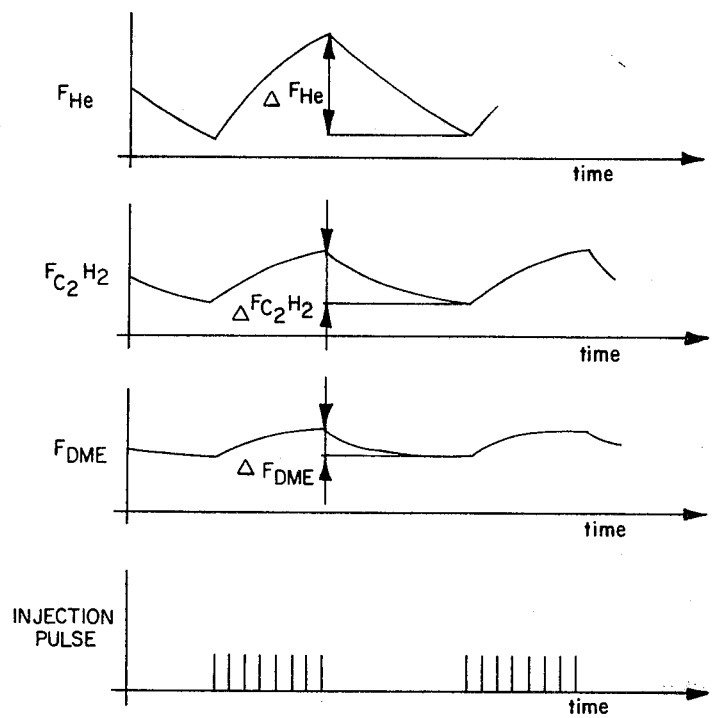
FIG. 4 is a plot of the cyclic alveolar gas fraction for three gases of varying solubility for cyclic periods of 8 breaths each.

As shown in FIG. 4, the $\Delta F$, which is the change in inert gas fraction in sampled expired air during a cycle will vary according to gas solubility. Helium has a Bunson solubility coefficient of essentially zero and hence produces a relatively high $\Delta F$. Acetylene has a solubility coefficient of 0.83 and has a smaller cyclic pattern. Dimethylether has a relatively large solubility of 9 and has even a flatter pattern. Thus, it may be seen that with increasing solubility, proportionately more tracer gas leaves the lung by the blood route than by ventilation resulting in the smaller cyclic patterns shown in FIG. 4. The venous return of the more soluble tracer gases increases the average level of the gas fraction in the sampled air but has little effect on the $\Delta F$ since the variation in the venous content is small over the cycle period. The relation of $\Delta F$ and the corresponding time constant $\tau$ of a given gas component to the ventilation-perfusion ratio and the lung volume are given mathematically as follows:

$$\Delta F_j = \frac{F_{Ij}}{1 + \lambda_j [\dot{Q}/\dot{V}]} \tanh \frac{T}{2\tau_j} \quad (1)$$

$$\tau_j = \frac{V'_j}{\dot{V}[1 + \lambda_j \dot{Q}/\dot{V}]} \quad (2)$$

$$V'_j = V + \lambda'_j V_T \quad (3)$$

where $\lambda_j$ is the blood solubility of the jth component, $\lambda'_j$ is the lung tissue solubility, T is the gas injection time period, $\dot{Q}/\dot{V}$ is the ventilation-perfusion ratio with subscripts removed for convenience, V is the average lung volume, $V_T$ is the tissue volume, and $V'_j$ is the total volume of the jth gas which includes average lung volume plus tissue gas volume. $F_{Ij}$ is the inspired gas fraction of the jth gas component.

The hyperbolic tangent factor approaches unity as the ratio of the insertion cycle period, T, to the time constant, $\tau_j$, becomes large. $\tau_j$ is determined from the data; its relationship to lung volume and the other parameters, as shown in equations (2) and (3) illustrates that lung volume is also a measured parameter of the system. For example, for an insoluble gas, equation (2) reduces to:

$$V = \tau_j \times \dot{V} \quad (4)$$

which is approximately equal to the parameter known to physiologists as FRC. Errors inherent from spontaneous but non-uniform breathing are greatly reduced by averaging the ΔF values over several cycles, providing a near continuous measure of the ventilation-perfusion ratio as given by equation (1), and lung volume (FRC) as given by equation (4).

The mathematical model given by equations (1) and (2) are representative of a single compartment lung (j represents two gases) which approximates a healthy lung. A multi-compartment model is required to approximate a diseased lung. Mathematically a non-uniform lung can be analyzed according to a multi-compartment model as follows:

$$\Delta F_j/F_{Ij} = \frac{1}{V} \sum_i \frac{V_i}{1 + \lambda_j \dot{Q}_i/\dot{V}_i} \tanh \frac{T}{2\tau_j} \quad (5)$$

where each compartment as labeled by the index i, is characterized by a unique ventilation-perfusion ratio. The equation (5) has the same mathematical form as described by Wagner, et al, in May of 1974 in their paper entitled, "Measurement of Continuous Distributions of Ventilation-Perfusion Ratios: Theory", published in the Journal of Applied Physiology 36:588–599. Representing the above mentioned distribution of this injection system as:

$$E_j = \frac{1}{V} \sum_i \frac{V_i}{1 + \dot{V}_i/\lambda_j \dot{Q}_i} \quad (6)$$

where $$E_j = \frac{F_j}{F_{\bar{v}j}} \quad (7)$$

$F_{\bar{v}j}$ is the jth gas fraction of central venous blood, and all other terms are as defined for equation (5).

More generally, equations (5) and (6) have the form:

$$Y_j = \sum_i \frac{X_i}{1 + a_{ij}} \quad (8)$$

where

| | |
|---|---|
| $Y_j = \dfrac{\Delta F_j}{\left(F_I \tanh \dfrac{T}{2\tau}\right)_j}$ | (from equation (5)) |
| $a_{ij} = \lambda_j \dot{Q}_i/\dot{V}_i$ | (from equation (5)) |
| $Y_j = \dfrac{F_j}{F_{\bar{v}j}}$ | (from equation (6)) |
| $a_{ij} = \dot{V}_i/\lambda_j \dot{Q}_i$ | (from equation (6)) |
| $X_i = V_i/V$ | (from equations (5) & (6)) |

In each case, $Y_j$ is the array of data obtained from gas analysis, $a_{ij}$ are $\dot{V}/\dot{Q}$ related parameters (values of which are assigned to each compartment), and the $X_i$ values are the unknowns which are explicitly solved using Wagner's mathematical algorithm and represent the distribution of ventilation as a function of ventilation-perfusion ratio. The present invention, therefore, uses the Wagner mathematical algorithm for solving equation (8) using current data for $Y_j$, using $a_{ij}$ values consistent with the assigned $\dot{V}/\dot{Q}$ of each compartment, and obtains a distribution of $\dot{V}_i/V$ values which have the same physiological meaning as those obtained by Wagner.

In summary, this invention utilizes a cyclic method of soluble and insoluble inertion gas insertion which essentially eliminates problems inherent in venous return, providing a near continuous and non-invasive means of measuring pulmonary blood flow and the distribution of ventilation as a function of the ventilation-perfusion ratio. The latter measurement is independent of other measurements, while the measurement of pulmonary blood (as well as FRC) requires the additional measurement of $\dot{V}_A$ by a method such as that described in U.S. Pat. No. 4,221,224.

Figure 5:
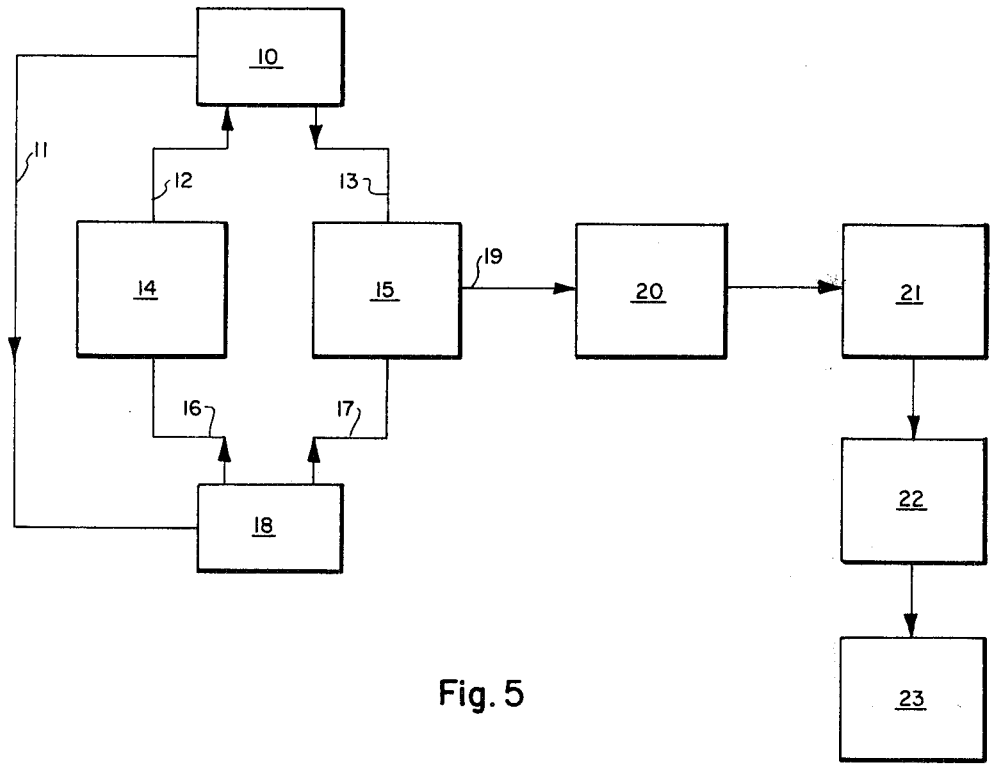
FIG. 5 is a block diagram of the cyclic injection, continuous sampling and pulmonary parameter analysis system.

The methods and apparatus used for injecting, sampling and analyzing gases to obtain pulmonary parameters may be any of a number used presently in the art. What is important is the novel cyclic means in which these methods and equipment are arranged and used. The preferred embodiment consists of utilization of the system taught in U.S. Pat. No. 4,221,224. FIG. 5 is a block diagram of the gas insertion sampling equipment, and analyzers according to the preferred embodiment. It is non-invasive and non-airtight due to the use of small tubes or catheters 12 and 13 which extend into each naris of a nose represented by block 10. Each naris is only partially blocked allowing for free breathing. One catheter 12 is used to inject the gases from source 14 and the other 13 is used to sample gas representative of alveolar air. For a patient on a respirator or other airtight apparatus, said injection method may still be used effectively, and it remains non-airtight because it allows for the free passage of air which is being controlled by the respirator or other airtight method. The bolus of injection gases consists of one insoluble gas such as helium which is injected on a cyclical basis throughout the sampling process. Once a cyclic steady state of helium concentration from the cyclical injections of helium is achieved, the alveolar ventilation $V_A$ can be determined as taught in U.S. Pat. No. 4,221,224, using the time average value of the measured helium gas fraction.

This same apparatus may be employed to inject both soluble and insoluble gases. The insoluble gas is used to determine alveolar ventilation ($\dot{V}_A$) as described and the soluble gases are used to obtain a result which is a function of $\dot{V}_A/\dot{Q}_c$. Since the injection of soluble gas(es) provides a concentration pattern which is a function of $\dot{V}_A/\dot{Q}_c$ and since $\dot{V}_A$ can be determined by the method disclosed in U.S. Pat. No. 4,221,224, the concentration of soluble gases injected is not critical as long as the analyzing instrumentation is sensitive enough to determine the gas fractions. On the other hand, the concentration of soluble gases must not exceed that which can be tolerated by the patient. For the sake of convenience and simplicity, it is preferred to inject a composite bolus of mixed tracer gases, including the insoluble gas, having known concentrations. The bolus of gas is injected at a given point in time after inhalation begins so that all of the inhaled gas enters the alveoli and none is left in the anatomical deadspace of the subject. Sampling time is also controlled by the use of a temperature sensitive thermistor in the tip of catheter 12 connected to a conventional microprocessor 18 by a signal line 11, so as to sample the gas representative of alveolar air and not air from the anatomical deadspace. The same method of timing injections and sampling according to each inhalation or exhalation used in U.S. Pat. No. 4,221,224 is employed in this cyclic injection system. The cyclical injections are done by continuing injections for a given number of breaths or given period of time followed by no injections for a given number of breaths or period of time to allow for a washout of the soluble gases previously injected. The cyclic injection pattern is controlled by the microprocessor 18 by signal line 16 leading to the injector 14 in response to signals received by microprocessor 18 from the thermistor via line 11. The gas dispensing device or injector 14 may be such as the one taught in U.S. Pat. No. 4,062,373. Sampling will occur so that data may be obtained both during injection as well as during washout. Each gas sample taken by the catheter 13 or tube inserted in the naris is interconnected to a gas collection system 15 and from the collector proceeds by syringe or other more direct means 19 to a mass spectrometer, gas chromatograph or other equipment for analyzing gas samples 20. The results obtained in the gas analyzer 20 can be relayed to a remote terminal 21 and into a computer 22 which determines not only alveolar ventilation but also obtains other pulmonary parameters due to the cyclic injection process 14 such as: pulmonary blood flow, the ventilation-perfusion distribution, and functional residual capacity which are then visually displayed or printed by display unit or printer 23.

The details of the timing of each injection upon inhalation and sampling upon exhalation are completely disclosed in U.S. Pat. No. 4,221,224. The injection system 14, however, is timed by controller 18 to the number of breaths, such as 8 breaths for example, so that injection of the bolus of gases is injected for each of 8 breaths. For the next 8 breaths, there are no injections to allow for a washout of the gases, thus providing the desired cyclic gas fraction pattern shown in FIG. 2, and thereby providing for a non-invasive, non-airtight, continuous means of monitoring and obtaining pulmonary parameters such as pulmonary blood flow, the ventilation-perfusion distribution, and functional residual capacity.

Typical of the soluble gases which may safely be injected into the airway of a patient according to this invention are Freon 12, acetylene, dimethylether, halothane, methyl chloride, acetone, ethane, methane, nitrous oxide, fluroxene and Freon 22. These gases are either inert or have been used as anesthetics. At the concentrations used, no anesthetic or other side effects have been observed. The maximum concentrations given as gas fractions are:

| | |
|---|---|
| Freon 12 | .01 |
| acetylene | .01 |
| dimethylether | .002 |
| halothane | .0001 |
| acetone | .0001 |
| methyl chloride | .0001 |
| ethane | .01 |
| methane | .01 |
| nitrous oxide | .01 |
| fluroxene | .0001 |
| Freon 22 | .01 |

I claim:

1. In a method of sampling and analyzing alveolar air is a human subject without requiring an airtight seal between the subject and monitoring equipment to determine alveolar ventilation by means of injecting a known amount of an insoluble inert tracer gas into the airway of a subject by non-airtight means, during inspiration and directly sampling expired alveolar air by non-airtight means and monitoring the inert tracer gas concentration in expired air under steady state conditions to determine alveolar ventilation, the improvement which consists of determining additional pulmonary parameters, comprising the steps of:
   (a) directly introducing the known amount of insoluble inert tracer gas during each inspiratory cycle for a given period of time designated as a washin cycle and then halting the introduction of such gas for a given period of time designated as a washout cycle,
   (c) simultaneous with the introduction of the insoluble tracer gas, introducing one or more additional tracer gases which are at least partially soluble in blood for the same washing cycle and then halting the introduction of said soluble tracer gas or gases for the same washout cycle,
   (c) continuously repeating said washin and washout cycles and sampling and monitoring the insoluble and soluble gas fractions in sampled expired alveolar air, and
   (d) utilizing the monitored data to determine the desired pulmonary parameter.

2. A method according to claim 1 wherein the sampled expired alveolar gases are monitored by means which create electronic signals which signals are relayed to translation means which convert said signals into visual values which indicate the desired pulmonary parameter.

3. A method according to claim 2 wherein the given period of time for each washin and washout cycle is a predetermined number of breaths.

4. A method according to claim 3 wherein the washin and washout cycles are continued for a multiplicity of cycles and wherein the monitored data is averaged over a given number of cycles before being utilized in determining the desired pulmonary parameters.

5. A method according to claim 4 wherein the said one or more gases which are at least partially soluble in blood are selected from the group consisting of ethane, methane, acetylene, nitrous oxide, methyl chloride, halothane, fluroxene, dimethylether, acetone, dichlorodifluoromethane, monochlorodifluoromethane and mixtures thereof.

6. A method according to claim 5 wherein a single gas, which is at least partially soluble in blood, is used.

7. A method according to claim 5 wherein a multiplicity of gases which are at least partially soluble in blood are used.

8. A method according to claim 5 wherein the predetermined number of breaths during the washin and washout cycles is between 1 and 30 inclusive.

9. A method according to claim 5 wherein the insoluble gas is a member selected from the group consisting of helium, argon, sulfurhexafluoride and carbon tetrafluoride.

10. A method for determining the ventilation-perfusion distribution in a human subject which comprises:
   a. directly introducing a gaseous mixture of tracer gases into the airway of said subject during each inspiratory cycle for a given period of time designated as a washin cycle and then halting the introduction of such mixture for a given period of time designated as a washout cycle, said gas consisting of one inert tracer gas which is relatively insoluble in blood and one or more inert tracer gases which are at least partially soluble in blood wherein the ratio of each soluble gas to the insoluble gas is known, b. continuously repeating said washin and washout cycles, c. sampling expired alveolar air from each cycle and monitoring the one or more ratios of said one or more soluble tracer gases to insoluble tracer gas in the sampled expired alveolar air, and d. utilizing the monitored data obtained from sampled alveolar air along with the known ratios of tracer gases cyclically introduced to determine ventilation-perfusion distribution.

11. A method according to claim 10 wherein the sampled expired alveolar gases are monitored by means which create electronic signals which signals are relayed to translation means which convert said signals into visual values which indicate the desired pulmonary parameter.

12. A method according to claim 11 wherein the given period of time for each washin and washout cycle is a predetermined number of breaths.

13. A method according to claim 12 wherein the washin and washout cycles are continued for a multiplicity of cycles and wherein the monitored data is averaged over a given number of cycles before being utilized in determining the ventilation-perfusion distribution.

14. A method according to claim 13 wherein the said one or more gases which are at least partially soluble in blood are selected from the group consisting of ethane, methane, acetylene, nitrous oxide, methyl chloride, halothane, fluroxene, dimethylether, acetone, dichlorodifluoromethane, monochlorodifluoromethane and mixtures thereof.

15. A method according to claim 14 wherein a multiplicity of gases which are at least partially soluble in blood are used.

16. A method according to claim 15 wherein predetermined number of breaths during the washin and washout cycles is between 1 and 30 inclusive.

17. A method according to claim 14 wherein the insoluble tracer gas is selected from the group consisting of helium, argon, sulfur hexafluoride, and carbon tetrafluoride.

* * * * *